United States Patent
Frushour et al.

(10) Patent No.: US 11,382,649 B2
(45) Date of Patent: Jul. 12, 2022

(54) ROTATION CONTROL SYSTEMS FOR SURGICAL INSTRUMENTS

(71) Applicant: COVIDIEN LP, Mansfield, MA (US)

(72) Inventors: Scott E. M. Frushour, Boulder, CO (US); Christopher A. Valentine, Boulder, CO (US)

(73) Assignee: Covidien LP, Mansfield, MA (US)

( * ) Notice: Subject to any disclaimer, the term of this patent is extended or adjusted under 35 U.S.C. 154(b) by 951 days.

(21) Appl. No.: 15/354,038

(22) Filed: Nov. 17, 2016

(65) Prior Publication Data
US 2018/0133521 A1    May 17, 2018

(51) Int. Cl.
| | | |
|---|---|---|
| A61B 17/32 | (2006.01) | |
| A61B 18/14 | (2006.01) | |
| A61B 17/00 | (2006.01) | |
| A61B 17/29 | (2006.01) | |
| A61B 90/00 | (2016.01) | |
| A61B 17/128 | (2006.01) | |
| A61B 17/064 | (2006.01) | |
| A61B 17/04 | (2006.01) | |

(52) U.S. Cl.
CPC .. *A61B 17/320092* (2013.01); *A61B 17/0469* (2013.01); *A61B 17/064* (2013.01); *A61B 17/1285* (2013.01); *A61B 18/1445* (2013.01); *A61B 2017/00017* (2013.01); *A61B 2017/00075* (2013.01); *A61B 2017/00398* (2013.01); *A61B 2017/2929* (2013.01); *A61B 2017/320093* (2017.08); *A61B 2017/320094* (2017.08); *A61B 2017/320095* (2017.08); *A61B 2090/031* (2016.02)

(58) Field of Classification Search
CPC .... A61B 2017/2946; A61B 2017/2903; A61B 17/2909; A61B 17/320092; A61B 18/1445
See application file for complete search history.

(56) References Cited

U.S. PATENT DOCUMENTS

| | | | |
|---|---|---|---|
| 4,503,842 A | 3/1985 | Takayama | |
| 5,350,355 A | 9/1994 | Sklar | |
| 6,872,178 B2 | 3/2005 | Weinberg | |
| 7,922,061 B2 | 4/2011 | Shelton, IV et al. | |
| 7,955,327 B2* | 6/2011 | Sartor | A61B 18/1402 606/45 |
| 8,419,717 B2 | 4/2013 | Diolaiti et al. | |
| 8,764,749 B2* | 7/2014 | McKenna | A61B 18/1442 606/51 |
| 2012/0221145 A1* | 8/2012 | Ogawa | A61B 34/37 700/259 |
| 2013/0123783 A1* | 5/2013 | Marczyk | A61B 17/29 606/45 |
| 2013/0324999 A1 | 12/2013 | Price et al. | |

(Continued)

*Primary Examiner* — Thomas A Giuliani
*Assistant Examiner* — Christine A Dedoulis
(74) *Attorney, Agent, or Firm* — Carter, DeLuca & Farrell LLP

(57) ABSTRACT

A surgical instrument includes a handle assembly, an elongate member, and a motor assembly. The elongate member extends from the handle assembly and defines a longitudinal axis of the surgical instrument. The motor assembly is disposed within the handle assembly and is configured to rotate the elongate member about the longitudinal axis relative to that handle assembly in response to sensed movement of the handle assembly about the longitudinal axis.

10 Claims, 3 Drawing Sheets

(56) References Cited

U.S. PATENT DOCUMENTS

2014/0246471 A1* 9/2014 Jaworek ............... A61B 17/068
                                                    227/175.1
2014/0303643 A1   10/2014 Ha et al.
2016/0302840 A1*  10/2016 Scheib ........... A61B 17/320092
2017/0172606 A1*   6/2017 Riestenberg ... A61B 17/320068

* cited by examiner

ROTATION CONTROL SYSTEMS FOR SURGICAL INSTRUMENTS

BACKGROUND

1. Technical Field

The present disclosure relates to surgical instruments and, more specifically, to endoscopic surgical instruments including rotation control systems that rotate an end effector of the surgical instrument.

2. Discussion of Related Art

Endoscopic instruments have become widely used by surgeons. Some endoscopic instruments incorporate rotation features, thus enabling rotation of an end effector relative to a handle assembly of the endoscopic instrument to a desired orientation within the surgical site. Generally, the rotation features of endoscopic instruments are manipulated by the finger of a surgeon. The rotation features allow a surgeon to manually rotate the end effector relative to the handle assembly of the endoscopic instrument. Such manual rotation of the end effector can result in fatigue or stress in the fingers of the surgeon.

SUMMARY

This disclosure relates generally to an endoscopic surgical instrument including a motor assembly that rotates an end effector of the surgical instrument in response to inputs of a clinician. The surgical instrument includes a motion sensing assembly that senses movement of a handle assembly of the surgical instrument from a home position and rotates the end effector in response to the sensed movement. Additionally or alternatively, the surgical instrument can include a rotation control that is engaged by a finger of a clinician to rotate the end effector relative to the handle assembly.

In an aspect of the present disclosure, a surgical instrument includes a handle assembly, an elongate member, and a motor assembly. The elongate member extends from the handle assembly and defines a longitudinal axis of the surgical instrument. The motor assembly is disposed within the handle assembly and is configured to rotate the elongate member about the longitudinal axis relative to that handle assembly in response to sensed movement of the handle assembly about the longitudinal axis.

In aspects, the surgical instrument includes a motion sensing assembly disposed within the handle assembly. The motion sensing assembly may be configured to sense rotational movement of the handle assembly relative to the longitudinal axis. The motor assembly may be configured to rotate the elongate member at a radial speed proportional to radial displacement of the handle from the home position. The motion sensing assembly can include a microcontroller that analyzes movement of the handle assembly within a gravitational field.

In some aspects, the surgical instrument includes a motion activation control that is engagable to define a home position about which the elongate member is rotatable relative to the handle assembly. The surgical instrument can include a rotation lockout that is configured to prevent rotation of the elongate member relative to the handle assembly in response to a condition of the surgical instrument. The surgical instrument can include an end effector supported on a distal end of the elongate member. The end effector can include at least one jaw that is moveable between open and clamping conditions. The rotation lockout can prevent rotation of the elongate member when the at least one jaw is in the clamping condition. The rotation lockout can include a lockout switch that is disposed in the end effector and is configured to sense when the at least one jaw of the end effector is in the closed configuration.

In certain aspects, the surgical instrument includes a clamp trigger that is configured to move the at least one jaw toward the closed configuration. The rotation lockout can include a lockout switch that is engaged by the clamp trigger when the clamp trigger is actuated. The rotation lockout can prevent rotation of the elongate member relative to the handle assembly in response to engagement of the lockout switch. The surgical instrument can include an activation button. The surgical instrument can be configured to deliver energy to the end effector in response to the activation button being depressed. The rotation lockout can include a lockout switch that is engaged by the activation button when the activation button is depressed. The rotation lockout can prevent rotation of the elongate member relative to the handle assembly in response to engagement of the lockout switch.

In another aspect of the present disclosure, a method of rotating an elongate member of a surgical instrument relative to a handle assembly of the surgical instrument includes rotating the handle assembly about a longitudinal axis in a first direction such that a motion sensing assembly, disposed within the handle assembly, senses movement of the handle assembly. The motion assembly affects rotation of the elongate member relative to the handle assembly about the longitudinal axis in the first direction in response to rotation of the handle assembly in the first direction.

In aspects, the method includes further rotating the handle assembly about the longitudinal axis in the first direction such that the motion sensing assembly increases a radial velocity of the rotation of the elongate member relative to the housing about the longitudinal axis in the first direction. Additionally or alternatively, the method can include rotating the handle assembly about the longitudinal axis in a section direction that is opposite to the first direction such that the motion sensing assembly stops rotation of the elongate member relative to the handle assembly about the longitudinal axis in response to rotation of the handle assembly in the second direction. The method can include further rotating the handle assembly about the longitudinal axis in the second direction such that the motion sensing assembly affects rotation of the elongate member relative to the handle assembly about the longitudinal axis in the second direction in response to the further rotation of the handle assembly in the second direction.

In another aspect of the present disclosure, a surgical instrument includes a handle assembly, an elongate member, a rotation control, and a motor assembly. The elongate member extends from the handle assembly and defines a longitudinal axis of the surgical instrument. The rotation control is disposed on the handle assembly. The motor assembly is disposed within the handle assembly and is configured to affect rotation of the elongate member about the longitudinal axis that is relative to the handle assembly in response to rotation of the rotation control.

In aspects, the rotation control is a potentiometer. The rotation control can be a return-to-center potentiometer. The motor assembly can rotate the elongate member about the longitudinal axis relative to the handle assembly at a radial speed in proportion to rotation of the rotation control about a control axis that is parallel to the longitudinal axis.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
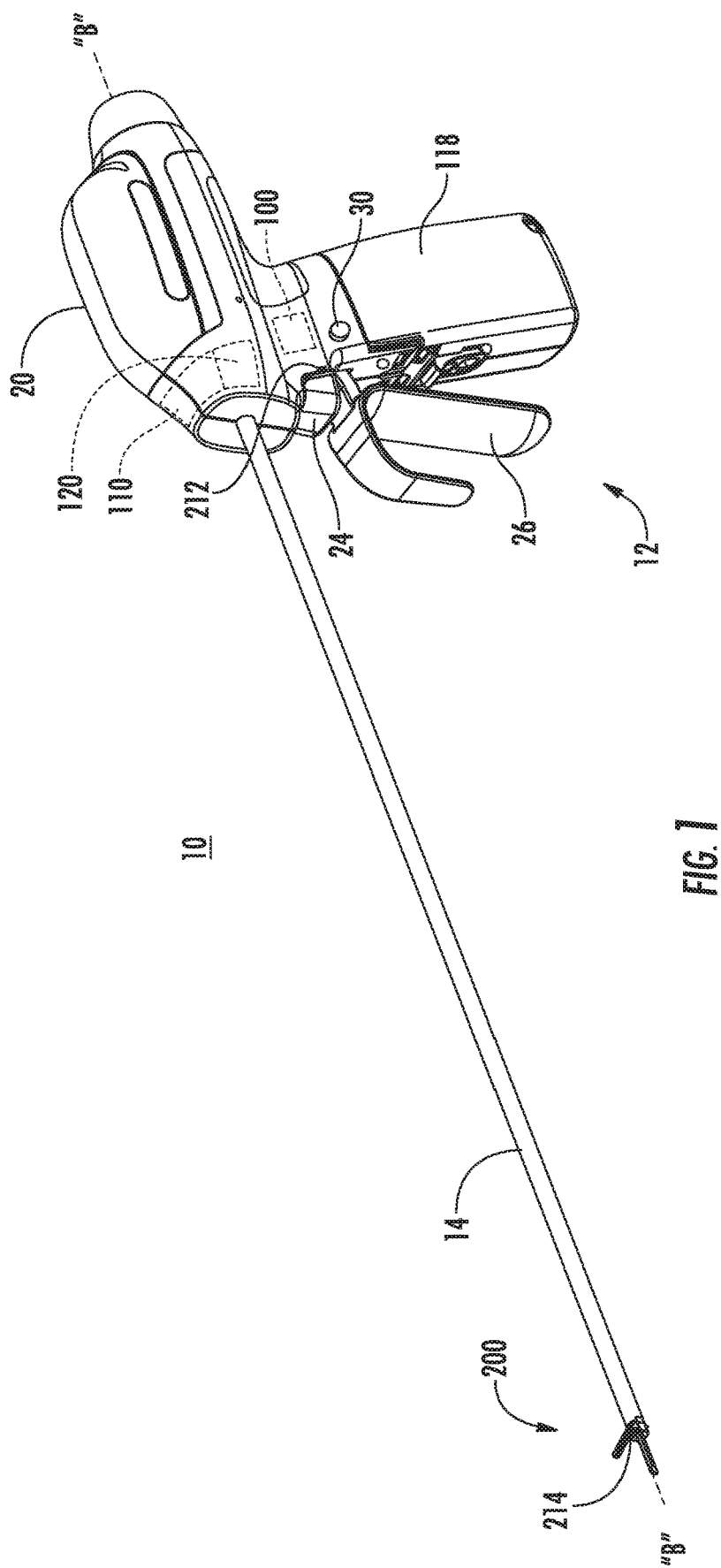
FIG. 1 is a perspective view of an endoscopic surgical instrument provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to an endoscopic surgical instrument including a motor assembly that rotates an end effector of the surgical instrument in response to inputs of a clinician. The surgical instrument can include a motion sensing assembly that senses movement of a handle assembly of the surgical instrument from a home position and rotates the end effector in response to the sensed movement. Additionally or alternatively, the surgical instrument can include a rotation control that is engaged by a finger of a clinician to rotate the end effector relative to the handle assembly.

Referring now to FIG. 1, an endoscopic surgical instrument exemplifying aspects and features of the present disclosure is shown generally identified by reference numeral 10. For the purposes herein, endoscopic surgical instrument 10 is generally described. Aspects and features of endoscopic surgical instrument 10 not germane to the understanding of the present disclosure are omitted to avoid obscuring the aspects and features of the present disclosure in unnecessary detail. As detailed herein, the endoscopic surgical instrument 10 is an ultrasonic surgical instrument configured to deliver ultrasonic energy to tissue; however, it is contemplated that an endoscopic surgical instrument in accordance with the present disclosure can be a surgical stapler, a surgical clip applier instrument, a surgical suturing instrument, an electrosurgical surgical instrument, etc.

The endoscopic surgical instrument 10 generally includes a handle assembly 12, an elongate member 14, a motion sensing assembly 100, and an ultrasonic surgical end effector 200 including a first jaw movable relative to an ultrasonic blade (or second jaw) between an open condition and a clamping condition. The handle assembly 12 supports a battery assembly 118 and a generator assembly 20, and includes an activation button 24 and a clamp trigger 26. The elongate member 14 defines a longitudinal axis B-B of the surgical instrument 10.

The clamp trigger 26 of the endoscopic surgical instrument 10 is selectively manipulatable to actuate a motor, other powered drive mechanism, or a manual drive mechanism, e.g., gears, pulleys, tension cables, etc., to transition the end effector 200 between the open condition and the clamping condition.

The battery assembly 118 and the generator assembly 20 cooperate, upon activation of the activation button 24, to supply power to the end effector 200 to enable the generation of ultrasonic energy for treating tissue therewith, e.g., to coagulate, cauterize, fuse, seal, cut, desiccate, fulgurate, or otherwise treat tissue, as detailed below. The battery assembly 118 and the generator assembly 20 are each releasably secured to the handle assembly 12, and are removable therefrom to facilitate disposal of the handle assembly 12, with the exception of the battery assembly 118 and the generator 20. However, it is contemplated that any or all of the components of the endoscopic surgical instrument 10 be configured as disposable single-use components or sterilizable multi-use components, and/or that the endoscopic surgical instrument 10 be connectable to a remote power source or generator rather than having such components on-board.

The motion sensing assembly 100, together with motor assembly 110, is configured to manipulate the end effector 200 in response to movement of the handle assembly 12. The handle assembly 12 can include a motion activation control 30 that activates the motion sensing assembly 100. When the motion activation control 30 is activated, the motion sensing assembly 100 creates a home or reference position corresponding to the position of the handle assembly 12 at that moment. This reference position is then stored in a memory of the motion sensing assembly 100. Once the reference position is stored, the motion sensing assembly 100 is able to detect movement of the handle assembly 12 relative to the reference position and direct the motor assembly 110 to manipulate the end effector 200 in response to movement of the handle assembly 12 relative to the reference position.

The motion sensing assembly 100 may include accelerometers, gyroscopes, and/or other suitable mechanisms configured to determine movement of the handle assembly 12 relative to the reference position within a gravitational field. The microcontroller of the motion sensing assembly 100 analyzes movement of the handle assembly 12 within the gravitational field and directs the motor assembly 110 to manipulate the end effector 200 in response to the movement of the handle assembly 12. A storage device associated with the microcontroller stores one or more programs for execution by the microcontroller to perform the above.

Figure 2:
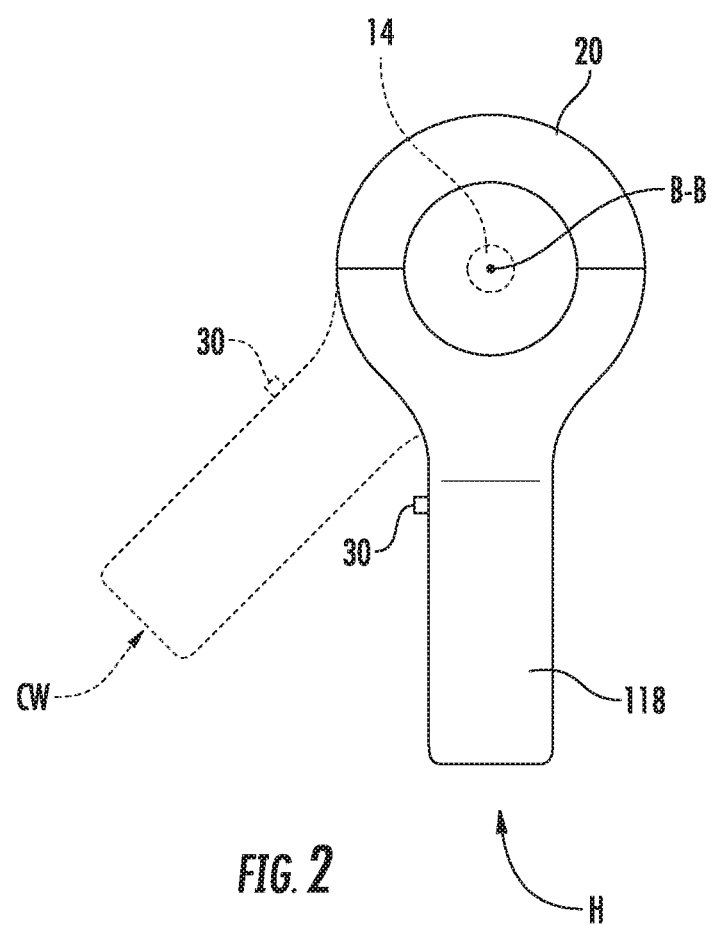
FIG. 2 is a rear view of the surgical instrument of FIG. 1.

With additional reference to FIG. 2, wherein the motion activation control 30 has been activated to register home position H, when the handle assembly 12 is rotated from the home position H about the axis B-B in a clockwise direction, towards position CW, the motor assembly 110 rotates the elongate body 14 about the axis B-B, which rotates the end effector 200, relative to the handle assembly 20 in a clockwise direction. As the radial displacement of the handle assembly 12 about the axis B-B is increased, the motor assembly 110 increases the speed at which the elongate body 14 is rotated about the axis B-B relative to the handle assembly 20. Similarly, as the radial displacement of the handle assembly 12 about the axis B-B is decreased, the motor assembly 110 decreases the speed at which the elongate body 14 is rotated about the axis B-B relative to the handle assembly 20. Position CW may represent a maximum angular speed of rotation of the elongate body 14 such that rotation beyond position CW ceases to increase the angular speed of rotation of the elongate body 14 relative to the handle assembly 20. As shown, the handle assembly 12 may reach the position CW after about π/4 or 45° of rotation; however, it is contemplated that position CW may be reached in a range of about π/6 or 30° to about π/2 or 90° of rotation. The maximum angular speed of rotation of the elongate body 14 may be in the range of about 5 rpm to about 30 rpm (e.g., about 15 rpm), although other speed of rotation ranges are also contemplated. It will be appreciated that speed of rotation of the elongate body 14 is proportional to the rotation of the handle assembly 12 about the axis B-B from the home position towards the position CW.

Similarly, when the handle assembly 12 is rotated from the home position H about the axis B-B in a counterclockwise direction, the motor assembly 110 rotates the elongate body 14 about the axis B-B, which rotates the end effector 200, relative to the handle assembly 20 in a counterclockwise direction.

Continuing to refer to FIGS. 1 and 2, the surgical instrument 10 may include a rotation lockout feature that can prevent rotation of the end effector 200 when certain conditions are met. For example, the rotation lockout feature can be configured to prevent rotation of the end effector 200 relative to the handle assembly 20 when energy, e.g., ultrasonic energy, electrosurgical energy, etc., is being delivered to the end effector 200. The rotation lockout feature may include a lockout switch 212 engagable by the activation button 24 such that when the activation button 24 is depressed, the lockout switch 212 signals to the microcontroller of the motion sensing assembly 100 to prevent rotation of the end effector 200 about the axis B-B relative to the handle assembly 20.

Additionally or alternatively, the rotation lockout feature may prevent rotation of the end effector 200 relative to the handle assembly 20 when the end effector 200 is in a closed or clamped configuration. The rotation lockout 210 may include a lockout switch 214 disposed in the end effector 200 such that as when the end effector 200 is in the clamping condition, the lockout switch 214 signals the microcontroller of the motion sensing assembly 100 to prevent rotation of the end effector 200 about the axis B-B relative to the handle assembly 20.

The surgical instrument 10 may also include a torque limiting mechanism 120 that prevents excessive torque from being applied by the motor assembly 110 to rotate the end effector 200 about the axis B-B relative to the handle assembly 20. The torque limiting mechanism 120 may be a mechanical coupler (e.g., a clutch) or an electronic limiter (e.g., a torque sensor in communication with the motor assembly 110). The torque limiting mechanism 120 may be positioned adjacent the motor assembly 110 or adjacent the end effector 200.

Figure 3:
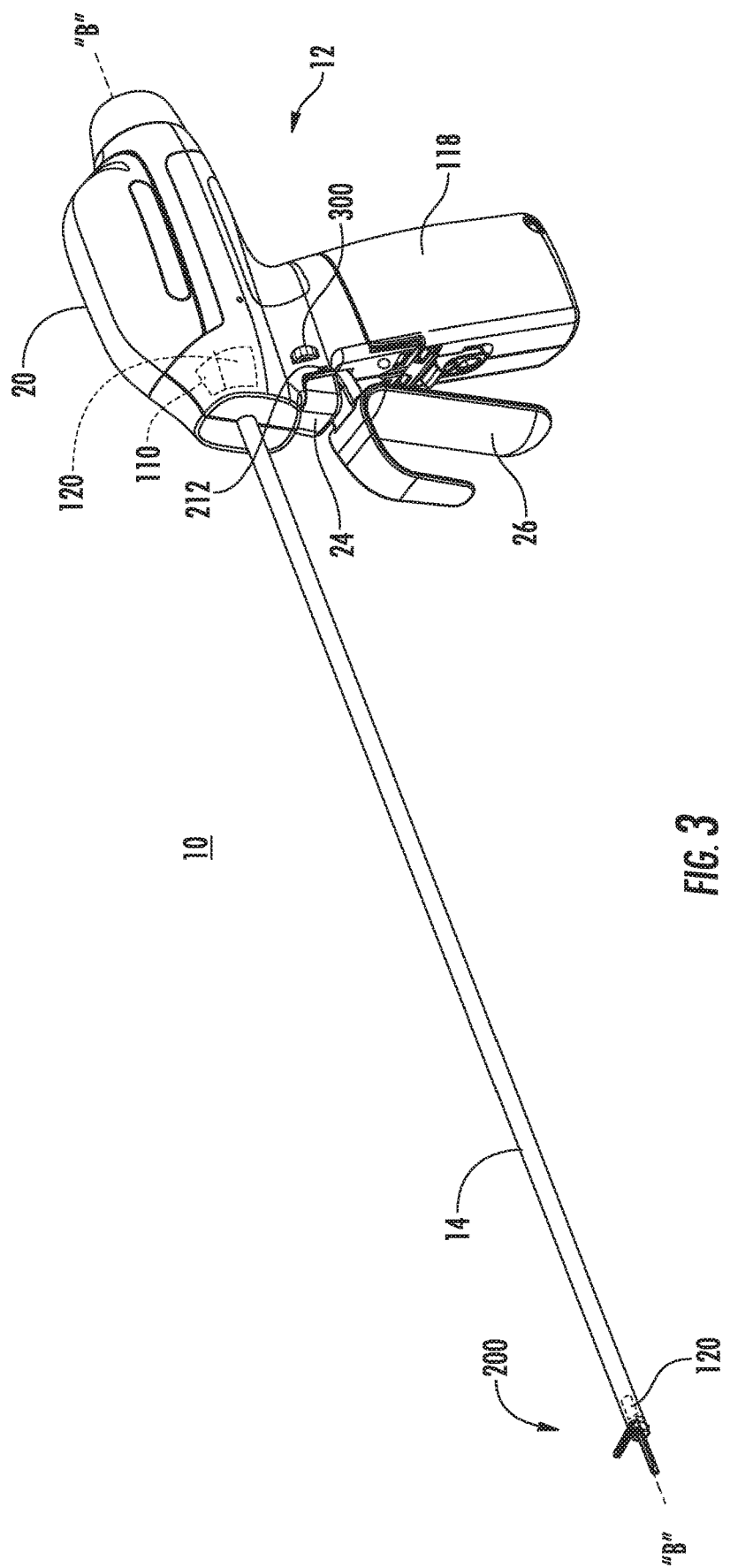
FIG. 3 is a perspective view of another endoscopic surgical instrument provided in accordance with the present disclosure.

Referring to FIG. 3, the endoscopic surgical instrument 10, as an alternative to motion sensing assembly 100 (FIG. 1), may include a rotation control 300 in accordance with the present disclosure. The rotation control 300 is disposed on the handle assembly 12 to control rotation of the elongate body 14 about the axis B-B relative to the handle assembly 20. The rotation control 300 can be in the form of a potentiometer that is engagable by the clinician such that rotation of the rotation control 300 in a clockwise direction directs motor assembly 110 to rotate the elongate body 14 about the axis B-B relative to the handle assembly 20 in a clockwise direction. It is contemplated that the rotation control 300 is rotatable about a control axis that is parallel to the axis B-B. It is envisioned that the motor assembly 110 rotates the elongate member 14 about the axis B-B relative to the handle assembly 20 at a radial speed proportional to the rotation of the rotation control 300 from the home position about the control axis.

Similarly, rotation of the rotation control 300 in a counterclockwise direction rotates the elongate body 14 about the axis B-B relative to the handle assembly 20 in a counterclockwise direction. The rotation control 300 may be a return-to-center potentiometer such that when the rotation control 300 is released, the rotation control 300 returns to a home or neutral position; the elongate body 14 is fixed about the axis B-B relative to the handle assembly 20 when the rotation control is in the neutral position. Rotation lockout features such as those detailed above may likewise be used in conjunction with rotation control 300.

It is contemplated that the rotation control 300 may be an encoder or a return-to-center encoder and function in a similar manner as detailed above with respect to a potentiometer and a return-to-center potentiometer, respectively. In embodiments where the rotation control 300 is an encoder or a return-to-center encoder, various methods of encoding input are contemplated including, but not limited to, electrical pulses or optics.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical instrument comprising:
    a handle assembly including a motion activation control configured to activate a motion sensing assembly disposed within the handle assembly;
    an elongate member extending from the handle assembly and defining a longitudinal axis of the surgical instrument, wherein the motion activation control establishes a reference position for the handle assembly as a reference radial orientation about the longitudinal axis that is occupied by the handle assembly at a moment when the motion sensing assembly is activated; and
    a motor assembly disposed within the handle assembly configured to rotate the elongate member about the longitudinal axis relative to the handle assembly in response to sensed radial movement, by the motion sensing assembly, of the handle assembly about the longitudinal axis relative to the reference position of the handle assembly within a gravitational field,
    wherein the motion sensing assembly is configured to sense radial displacement of the handle assembly about the longitudinal axis relative to the reference radial orientation,
    wherein a rotational speed of the elongate member is proportional to the radial displacement of the handle assembly relative to the reference radial orientation, and
        wherein a maximum rotational speed of the elongate member corresponds to a predefined radial orientation, such that radial displacement beyond the predefined radial orientation does not increase the rotational speed of the elongate member.

2. The surgical instrument according to claim 1, wherein the motion sensing assembly includes a microcontroller that analyzes movement of the handle assembly relative to the longitudinal axis within the gravitational field.

3. The surgical instrument according to claim 1, further comprising a rotation lockout configured to prevent rotation of the elongate member relative to the handle assembly in response to a condition of the surgical instrument.

4. The surgical instrument according to claim 3, further comprising an end effector supported on a distal end of the elongate member, the end effector including at least one jaw that is movable between an open condition and a clamping condition, the rotation lockout preventing rotation of the elongate member when the at least one jaw is in the clamping condition.

5. The surgical instrument according to claim 4, wherein the rotation lockout includes a lockout switch disposed in the end effector and configured to sense when the at least one jaw of the end effector is in the closed configuration.

6. The surgical instrument according to claim 4, further comprising a clamp trigger configured to move the at least one jaw toward the closed configuration, the rotation lockout including a lockout switch engaged by the clamp trigger when the clamp trigger is actuated, the rotation lockout preventing rotation of the elongate member relative to the handle assembly in response to engagement of the lockout switch.

7. The surgical instrument according to claim 3, further comprising an activation button, the surgical instrument configured to deliver energy to the end effector in response to the activation button being depressed, the rotation lockout including a lockout switch engaged by the activation button when the activation button is depressed, the rotation lockout preventing rotation of the elongate member relative to the handle assembly in response to engagement of the lockout switch.

8. A method of rotating an elongate member of a surgical instrument relative to a handle assembly of the surgical instrument, the method comprising:
   activating a motion sensing assembly within a handle assembly in response to activation of a motion activation control within the handle assembly;
   establishing a reference position for the handle assembly based on a reference radial orientation about a longitudinal axis defined by the elongate member occupied by the handle assembly at a moment when the motion sensing assembly is activated; and
   radially displacing the handle assembly about the longitudinal axis in a first direction relative to the reference radial orientation such that the motion sensing assembly senses the radial displacement of the handle assembly about the longitudinal axis relative to the reference radial orientation of the handle assembly within a gravitational field, the motion sensing assembly affecting rotation of the elongate member relative to the handle assembly about the longitudinal axis in the first direction in response to the radial displacement of the handle assembly in the first direction,
      wherein a rotational speed of the elongate member is proportional to the radial displacement of the handle assembly relative to the reference radial orientation, and
      wherein a maximum rotational speed of the elongate member corresponds to a predefined radial orientation, such that radial displacement beyond the predefined radial orientation does not increase the rotational speed of the elongate member.

9. The method according to claim 8, further comprising further rotating the handle assembly about the longitudinal axis in the first direction, the motion sensing assembly increasing a radial velocity of the rotation of the elongate member relative to the housing assembly about the longitudinal axis in the first direction in response to the further rotation of the handle assembly in the first direction.

10. The method according to claim 8, further comprising rotating the handle assembly about the longitudinal axis in a second direction opposite the first direction, the motion sensing assembly stopping rotation of the elongate member relative to the handle assembly about the longitudinal axis in response to rotation of the handle assembly in the second direction.

* * * * *